(12) United States Patent
Ooi et al.

(10) Patent No.: US 10,591,570 B2
(45) Date of Patent: Mar. 17, 2020

(54) METHOD FOR 3D MOTION TRACKING IN AN MRI SCANNER USING INDUCTIVELY COUPLED MICROCOILS

(71) Applicant: The Board of Trustees of the Leland Stanford Junior University, Palo Alto, CA (US)

(72) Inventors: Melvyn B. Ooi, College Station, TX (US); Julian Maclaren, Menlo Park, CA (US); Murat Aksoy, Menlo Park, CA (US); Roland Bammer, Palo Alto, CA (US); Ronald D. Watkins, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 736 days.

(21) Appl. No.: 14/109,403

(22) Filed: Dec. 17, 2013

(65) Prior Publication Data

US 2014/0171784 A1    Jun. 19, 2014

Related U.S. Application Data

(60) Provisional application No. 61/738,086, filed on Dec. 17, 2012.

(51) Int. Cl.
*G01R 33/563* (2006.01)
*G01R 33/565* (2006.01)
(Continued)

(52) U.S. Cl.
CPC ........ *G01R 33/56509* (2013.01); *A61B 5/055* (2013.01); *A61B 5/1114* (2013.01);
(Continued)

(58) Field of Classification Search
CPC .. A61B 5/055; A61B 5/6803; G01R 33/56509
See application file for complete search history.

(56) References Cited

U.S. PATENT DOCUMENTS

| 5,274,332 A | 12/1993 | Jaskolski et al. |
| 5,307,808 A | 5/1994 | Dumoulin et al. |

(Continued)

FOREIGN PATENT DOCUMENTS

WO    WO 2012/160486    11/2012

OTHER PUBLICATIONS

Burl et al., "Tuned fiducial markers to identify body locations with minimal perturbation of tissue magnetization", 1996, pp. 491-493, Magnetic Resonance in Medicine v36.
(Continued)

*Primary Examiner* — Rochelle D Turchen
(74) *Attorney, Agent, or Firm* — Lumen Patent Firm (57) ABSTRACT

Wireless markers having predetermined relative positions with respect to each other are employed for motion tracking and/or correction in magnetic resonance (MR) imaging. The markers are inductively coupled to the MR receive coil(s). The correspondence between marker signals and markers can be determined by using knowledge of the marker relative positions in various ways. The marker relative positions can be known a priori, or can be obtained from a preliminary scan. This approach is applicable for imaging (both prospective and retrospective motion correction), spectroscopy, and/or intervention.

19 Claims, 5 Drawing Sheets

(51) Int. Cl.
  *A61B 5/11* (2006.01)
  *A61B 5/055* (2006.01)
  *A61B 5/00* (2006.01)
  *G01R 33/58* (2006.01)

(52) U.S. Cl.
  CPC .......... *A61B 5/1127* (2013.01); *A61B 5/1128* (2013.01); *A61B 5/0037* (2013.01); *A61B 5/6803* (2013.01); *G01R 33/58* (2013.01)

(56) References Cited

U.S. PATENT DOCUMENTS

| | | | |
|---|---|---|---|
| 5,318,025 A | 6/1994 | Dumoulin et al. | |
| 5,947,900 A | 9/1999 | Derbyshire et al. | |
| 6,163,723 A * | 12/2000 | Roberts | A61N 1/36585 607/18 |
| 7,609,063 B2 | 10/2009 | Xue et al. | |
| 2003/0092981 A1 * | 5/2003 | Deimling | A61B 5/055 600/410 |
| 2005/0049486 A1 * | 3/2005 | Urquhart | A61B 34/20 600/429 |
| 2006/0036154 A1 * | 2/2006 | Deimling | G01R 33/5613 600/410 |
| 2007/0080685 A1 * | 4/2007 | Bydder | G01R 33/561 324/309 |
| 2007/0156042 A1 | 7/2007 | Unal | |
| 2008/0221431 A1 * | 9/2008 | Steinmeyer | G01R 33/287 600/414 |
| 2010/0013482 A1 * | 1/2010 | Baldo | G01R 33/58 324/318 |
| 2011/0257516 A1 | 10/2011 | Celik et al. | |
| 2014/0077811 A1 * | 3/2014 | Lin | A61B 5/055 324/309 |

OTHER PUBLICATIONS

Busse et al., "Method for automatic localization of MR-visible markers using morphological image processing and conventional pulse sequences: Feasibility for image-guided procedures", 2007, pp. 1087-1096, Journal of Magnetic Resonance Imaging v26.

Derbyshire et al., "Dynamic scan-plane tracking using MR position monitoring", 1998, pp. 924-932, Journal of Magnetic Resonance Imaging v8.

Dumoulin et al., "Real-time position monitoring of invasive devices using magnetic resonance", 1993, pp. 411-415, Magnetic Resonance in Medicine v29.

Flask et al., "A method for fast 3D tracking using tuned fiducial markers and a limited projection reconstruction FISP (LPR-FISP) sequence", 2001, pp. 617-627, Journal of Magnetic Resonance Imaging v14.

Ooi et al, "Prospective real-time correction for arbitrary head motion using active markers", 2009, pp. 943-954, Magnetic Resonance in Medicine v62.

Quick et al., "Interventional magnetic resonance angiography with no strings attached: Wireless active catheter visualization", 2005, pp. 446-455, Magnetic Resonance in Medicine v53.

Schnall et al., "Wireless implanted magnetic resonance probes for in vivo NMR", 1986, pp. 161-167, Journal of Magnetic Resonance v68.

* cited by examiner

FIG. 3B physical gradient axes

METHOD FOR 3D MOTION TRACKING IN AN MRI SCANNER USING INDUCTIVELY COUPLED MICROCOILS

CROSS REFERENCE TO RELATED APPLICATIONS

This application claims the benefit of U.S. provisional patent application 61/738,086, filed on Dec. 17, 2012, and hereby incorporated by reference in its entirety.

GOVERNMENT SPONSORSHIP

This invention was made with Government support under contract number EB011654 awarded by the National Institutes of Health. The Government has certain rights in this invention.

FIELD OF THE INVENTION

This invention relates to motion tracking in magnetic resonance (MR) imaging.

BACKGROUND

Motion is still an unsolved problem in magnetic resonance (MR) imaging and is a dominant source of artifacts. Motion often results in prolonged or diagnostically inadequate studies. This can lead to considerably lower diagnostic confidence or even incorrect diagnoses. To overcome motion, sedation or general anesthesia are sometimes required, which can add extra risk factors to the procedure. Moreover, the decreased patient comfort and throughput is inconvenient for both the patient and the clinicians, and can add significantly to overall exam/health care costs. Providing an accurate and reliable 3D motion tracking device is key for many prospective or retrospective motion correction approaches.

One approach for MR motion tracking that has been considered in the art is the use of wireless markers as fiducials for motion tracking, e.g., as considered by Flask et al. (JMRI 14:617-627, 2001). In such approaches there are several markers each providing signals to a common output (e.g., the MR receive coils), and it is necessary to determine the correspondence between markers and marker signals in order to use the markers for motion tracking. Various approaches for this have been considered in the art, such as tomographic reconstruction, but the correspondence problem remains a source of difficulty for conventional motion tracking with wireless markers.

SUMMARY

The present approach is mainly based on the use of a set of wireless markers having predetermined relative positions, where determination of the correspondence between markers and marker signals relies on knowledge of the predetermined relative positions of the markers.

An exemplary method for tracking the position and/or orientation of an object in a magnetic resonance (MR) imaging system includes the following steps.

1) Disposing two or more markers having predetermined relative positions on the object. Here the markers each include an MR-visible sample coupled to a resonant circuit, and the resonant circuits of the markers are inductively coupled to one or more receive coils of the MR imaging system.

2) Providing one or more navigator tracking pulses in an MR pulse sequence.

3) Receiving marker signals from the markers via the one or more receive coils, where the marker signals are responsive to the one or more navigator tracking pulses.

4) Determining a correspondence between the received marker signals and the markers such that the marker responsible for each received marker signal is determined, where determination of the correspondence relies on knowledge of the predetermined relative positions of the markers. This correspondence provides position and/or orientation information of the object.

5) Providing the position and/or orientation information of the object as an output or as an input for further processing.

Several ways to address the correspondence problem are described below. The markers can be substantially separated by distance from each other in each of three orthogonal directions. Here the knowledge of the predetermined relative positions of the markers is used to determine the correspondence from marker signal peak order. This approach is described in greater detail below in the detailed description.

Another approach for determining the correspondence is to determine a set of possible marker locations (e.g., by back projecting the marker signals in three orthogonal directions) and then determining the correspondence by matching these possible marker locations to a constellation of points having the predetermined relative positions of the markers. For example, if there were four markers having a generally tetrahedral arrangement on the tracking device, the constellation of points would be the vertices of this tetrahedron. The search would be for four possible marker locations that match this constellation, allowing translation and rigid rotation of the constellation as degrees of freedom in the search.

A further approach for determining the correspondence is applicable in cases where there is more than one MR receive coil, and/or the MR receive coil is a coil array that is composed of more than one coil array element. Here the knowledge of the predetermined relative positions of the markers can be used in combination with the known geometrical layout and sensitivity of the coil array, such that the marker signal from a given marker appears the largest in the coil array elements that are closest to it. Thus the received signal strength of each marker, as seen by each element of the coil array, can provide information on the relative distance between each marker and coil array element in order to determine the correspondence. For example, the largest received marker signal from an individual coil array element may be weighted to correspond to a specific marker, based on the proximity of the coil array element to the marker. Other characteristics of the received marker signal from an individual coil array element that may be analyzed include its magnitude, frequency, and/or phase.

In some cases (e.g., determining the correspondence from marker signal peak order), the approach for solving the correspondence problem relies on rotations seen in practice having a limited range. The range of rotations over which such approaches can work can be increased by performing prospective motion correction of the navigator tracking pulses to keep a relative orientation of coordinates of the navigator tracking pulses and the tracking device within a predetermined range. In one exemplary method, the markers need only be minimally separated by distance from each other in each of three orthogonal directions, and the knowledge of the predetermined relative positions of the markers is used to determine the correspondence from marker signal peak order. In addition, performing prospective motion correction of the navigator tracking pulses keeps a relative orientation of coordinates of the navigator tracking pulses and the tracking device within a predetermined range, such that the marker signal peak order does not change regardless of the magnitude of motion. Therefore, there is no limit to the range of motion that can be tracked.

The knowledge of the predetermined relative positions of the markers can be provided a priori (e.g., from the known dimensions and fixed marker locations on a tracking device). Alternatively, the knowledge of the predetermined relative positions of the markers can be provided by performing a preliminary scan of the markers. For example, a computed-tomography like acquisition and reconstruction of the marker positions can be performed in this preliminary scan, using multiple back projections. Alternatively, an image-based acquisition and reconstruction can be performed in this preliminary scan, followed by morphological image processing, in order to determine the marker positions. Additionally, knowledge of the marker positions obtained from the preliminary scan can be used to optimize the orientation and/or number of navigator tracking pulses to be used during the actual scan for tracking the object. For example, projections can be selected to maximize marker signal peak separation.

Practice of the invention does not depend critically on details of the navigator tracking pulses. Suitable navigator tracking pulses include, but are not limited to: gradient echo pulses, spin echo pulses, free induction decay pulses, zero echo time pulses, and pulses having an echo time of 1 ms or less.

The marker signals are preferably suppressed during parts of the MR pulse sequence that relate to MR imaging. There are various ways to accomplish this. 1) The markers can each include two diodes connected in parallel with opposite polarities and connected to the resonant circuit such that voltage across elements of the resonant circuit of the markers is limited. 2) The MR-visible samples of the markers can have a T2 relaxation time of less than 10 ms. 3) The MR-visible samples of the markers can have a proton density less than the proton density of tissue being imaged. 4) The MR-visible sample can have a different resonant frequency than the resonant frequency of tissue being imaged. In this manner, the wireless marker signal may also be selectively saturated at the end of each navigator tracking pulse. 5) The quality factor of the resonant circuits of the markers can be reduced during the parts of the MR pulse sequence that relate to MR imaging.

This approach is broadly applicable to any use of MR imaging and/or spectroscopy. In particular, it has applications for both imaging and intervention. For imaging, the object being tracked is a subject being imaged. The markers can be affixed to a tracking device substrate. Suitable tracking device substrates for this application include but are not limited to: head-mountable devices, headgear, glasses, goggles, headbands, and headphones. Due to their small size and wire-free operation, the wireless markers may be easily clipped onto existing headwear or alternative tracking devices, or directly integrated into a custom headwear/device design. The goggles or glasses design can be expanded to incorporate a video display system for entertainment or visual stimulus presentation. Here we focus mainly on the head because the head is a body part that moves as a rigid body, unlike most other body parts. However, the present approach can also be used to track any other body part in an MR system, and the tracking device substrates in such cases can include anything that can be worn or affixed (temporarily) to the body of a subject being imaged. Furthermore, a tracking device substrate is optional, since the markers could be placed on the subject directly (e.g., using double sided tape). The position and/or orientation information of the object provided by this motion tracking can be used to perform prospective and/or retrospective motion correction for MR imaging. If three or more markers are used, then motion tracking and/or correction can be performed for all six degrees of freedom of rigid-body motion (three translations and three rotations); if two markers are used, then motion tracking and/or correction can be performed for five degrees of freedom (three translations and two rotations).

For intervention, the object being tracked is an interventional device. Exemplary interventional devices include but are not limited to: a needle, a catheter, and a surgical instrument. The position and/or orientation information of the object provided by this motion tracking can be used to perform MR guided intervention.

The use of miniature RF coils for motion tracking has been previously established using "wired markers", where each RF coil is connected to the scanner via a traditional electrical cable. A wireless marker based approach has several advantages over the wired methods previously reported: 1) improved patient safety by eliminating the long, electrically conducting wires which are a potential source of RF heating and local SAR increase; 2) no additional RF receive channels are needed, since the tracking signal is detected via inductive coupling to the imaging RF coil; 3) improved tracking accuracy by removing the cables and any tracking errors caused by tugging on the cables; 4) importantly, because of their small size and wire-free operation, a wireless-marker tracking device will be easy to use, thereby facilitating their portability to a high-throughput clinical setting.

DETAILED DESCRIPTION

A) Introduction

Head motion is a fundamental problem for all in vivo brain MRI applications that, if left unaccounted for, can result in high clinical and public health costs. Even a few millimeters of movement can produce severe motion artifacts that can mask subtle lesions, obscure pathologies, or simply lower diagnostic confidence. A motion correction solution has yet to be demonstrated that is comprehensive, simple to deploy, and widely accepted in the clinic.

The use of miniature radio-frequency (RF) coils as position-tracking probes has been the foundation of several recent advances in prospective real-time motion correction. We refer to these previously developed RF coils as "wired markers", since each RF coil was connected to the scanner via a traditional coaxial cable. In our previous works, subjects wore a headband containing three wired markers, which served as the fiducial for head motion tracking. Prospective correction for rigid head motions, using the real-time tracking data from the wired markers, was successfully implemented in a variety of imaging sequences. The technique improved the image quality of 2D/3D structural MRI, as well as increased the statistical significance of functional MRI. While wired markers have been effective in a research setting, their widespread adoption may be hampered by the cables connecting the headband to the scanner, which would interfere with the regular clinical workflow.

We therefore introduce a novel RF coil-based "wireless marker" approach for prospective motion correction of brain MRI, which aims to streamline the overall setup procedure. All cable connections to the scanner are eliminated by inductively coupling the wireless markers to the imaging head-coil. Real-time tracking of rigid head motion has been performed using a pair of glasses, with three wireless markers integrated into its frame in a predefined geometrical arrangement. A tracking pulse-sequence, combined with knowledge of the markers' geometrical arrangement, is used to measure their positions. The wireless tracking data from the glasses is then used to prospectively update the orientation and position of the imaging volume so that it follows the motion of the head. Inductively coupled RF coils have been previously used to improve local image SNR, and to visualize stents and catheters.

The removal of all cables makes wireless markers substantially easier to use and less cumbersome than wired markers, thereby improving patient comfort, technologist setup times, and tracking fidelity. Patient safety is improved by eliminating the long, electrically conducting cables that are a potential source of RF heating and local SAR increase. Also, by inductively coupling the wireless markers to the imaging head-coil, the load on the scanner is reduced since no additional RF receiver channels or scanner interface circuitry is required. These practical advantages allow the technique to be more easily deployed in a high throughput clinical setting.

B) Methods

Experiments were performed on a 3T GE-MR750 scanner (GE Healthcare, WI). A standard eight-channel head-coil was used for imaging and inductive coupling to the wireless markers. All experiments with human subjects were in accordance with local institutional review board regulations and informed consent was obtained before each exam.

B1) Wireless Marker Device

Figure 1:
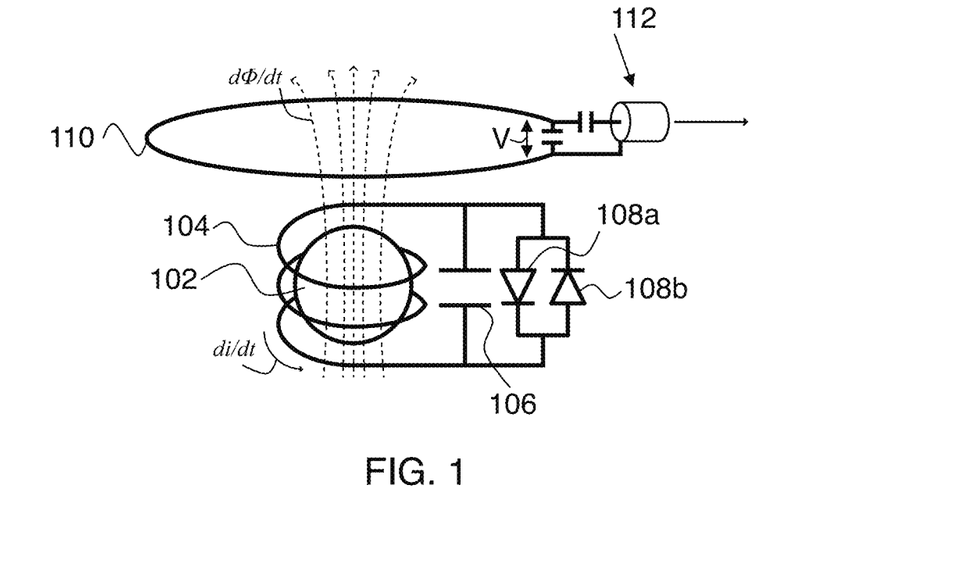
FIG. 1 schematically shows operation of wireless markers in an MR system.

FIG. 1 is a circuit schematic of a single wireless marker (bottom), and illustration of wireless-marker signal transmission by inductively coupling the wireless marker to the imaging coil 110 (in this example, coil 110 is a head-coil). The underlying principle used for wireless-marker tracking is Faraday's law of mutual induction. During RF receive, each wireless marker picks up the MR signal in its immediate vicinity (dominated by the spherical sample 102). The signal generates a current di/dt in the wireless marker (more specifically in coil 104), and an associated magnetic field (dashed lines) and flux dΦ/dt as it passes through the imaging head-coil 110. The flux induces a voltage V in the imaging head-coil according to Faraday's law: $di/dt \propto d\Phi/dt \propto V$, which is then routed to the standard RF receiver via wired connection 112. The key concept here is that even though RF coils 104 and 110 are not physically connected, the signal from the wireless marker is transmitted to the imaging head-coil via the magnetic flux dΦ/dt that links the two coils.

Prospective correction is performed using three wireless markers in order to uniquely define any six degrees-of-freedom rigid-body motion. In this work, each wireless marker (FIG. 1) includes a miniature RF coil 104 that is free of any mechanical connections to the scanner. Coil 104 is a three-turn (Ø~4 mm) solenoid inductor, and the marker also includes capacitor 106. This resonant circuit is tuned to 128 MHz because the scanner field strength was 3T for this work. Inside the solenoid cavity is a small glass sphere (Ø~3 mm) filled with Gd-doped water solution (10 mM). The spherical sample is the point source that is tracked. A fast-switching crossed diode 108a and 108b (UMX9989AP, Microsemi, Mass.) passively detunes the resonant circuit during RF transmit.

In the absence of any cable connections, wireless-marker signal transmission is achieved by inductively coupling the wireless markers to the nearby imaging head-coil. This is illustrated in FIG. 1. During RF receive, each wireless marker acts as a local signal amplifier that picks up the MR signal in its immediate vicinity, which is dominated by the spherical sample. The signal is then wirelessly transmitted to the imaging head-coil via the magnetic flux dΦ/dt that links the two coils, and thereby routed to the standard RF receiver.

Each wireless marker in this experiment was encased in a self-contained polycarbonate capsule. For phantom experiments, three capsules were rigidly attached to the phantom in a predefined geometrical arrangement. For in vivo experiments, the subject wore a pair of polycarbonate glasses (FIG. 3C) that was custom designed and 3D-printed (Stratasys Fortus 360 mc, MN) with three capsules integrated into its frame as described in greater detail below.

B2) Wireless Tracking Signal

Figure 2A:
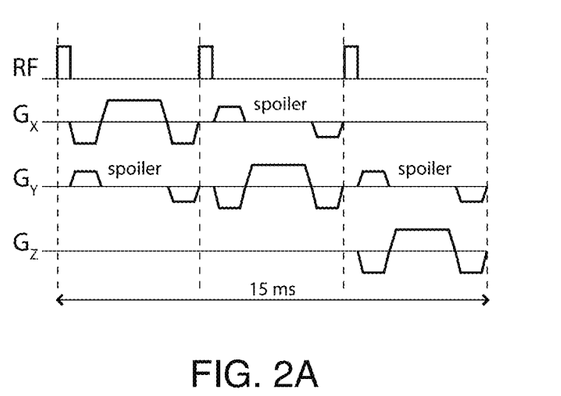
FIG. 2A shows an exemplary navigator pulse sequence.

Wireless marker positions were measured using the tracking pulse-sequence in FIG. 2A, which produces three 1D projections along the physical x, y, and z gradient axes. We refer to the signal from these 1D projections as the wireless tracking signal $S_{1-8}$, since the signal from all three markers is wirelessly received by the eight-channel head coil (receiver channels one to eight) via the inductive coupling mechanism. $S_{1-8}$ is calculated from the sum-of-squares signal over all eight channels. $S_{1-8}$ from a single x-projection of three markers (FIG. 2B) clearly shows three peaks, which correspond to the marker locations along the physical x-axis. A similar set of peaks in the y- and z-projections provides information on the marker positions in 3D.

Figure 2B:
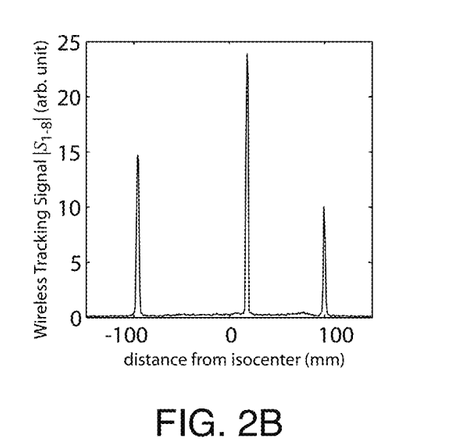
FIG. 2B shows an exemplary received marker signal.

FIG. 2A shows the tracking pulse-sequence used to measure wireless marker positions. A non-selective RF-pulse (α=1°) is followed by gradient-echo readouts along the physical x, y, and z gradient axes (FOV=300 mm, N=256), resulting in three 1D projections along orthogonal axes. Spoiler gradients dephase the magnetization in large volumes (from the subject) while preserving signal from the smaller spherical samples inside each marker. FIG. 2B shows the wireless tracking signal $S_{1-8}$ from three wireless markers after the x-projection of the tracking pulse-sequence. Three peaks are clearly visible, which correspond to the marker locations along the x-axis. Background signal from the phantom is well suppressed by the spoilers.

However, from $S_{1-8}$ alone it is not immediately apparent which peak corresponds to which marker, since the signals from all three markers are simultaneously coupled to the head coil. We refer to this peak-to-marker assignment as the "correspondence problem". Note that in previous works where position tracking of multiple wired markers was performed, each wired marker was directly connected to its own independent receiver channel. The signal from each wired marker was therefore separately and unambiguously identified, and so no correspondence problem existed. However, in the current work, in order to use $S_{1-8}$ for position tracking of multiple wireless markers, the correspondence problem must first be solved.

B3) the Peak-to-Marker Correspondence Problem

Figure 3A:
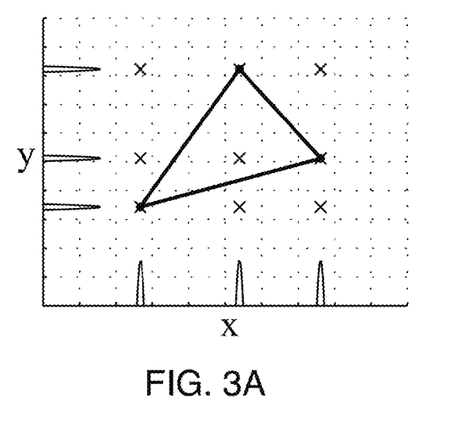
FIGS. 3A-B illustrate the correspondence problem.
Figure 3B:
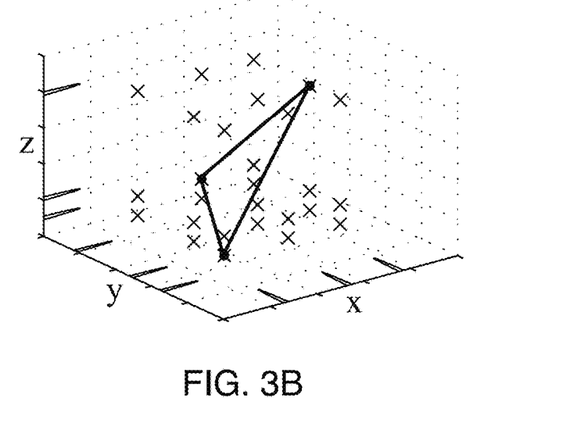
Figure 3C:
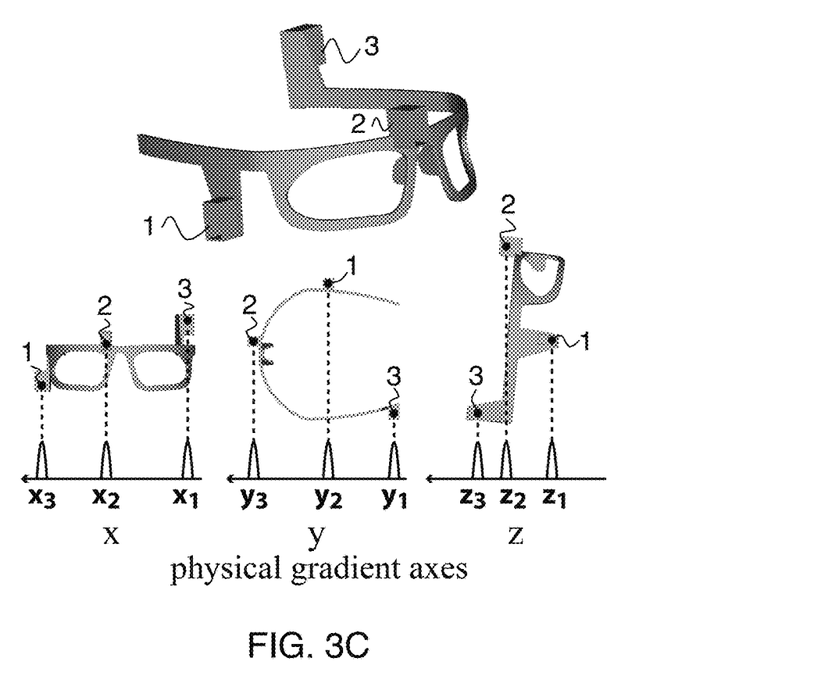
FIG. 3C shows one approach for solving the correspondence problem.

FIGS. 3A-C show the peak-to-marker correspondence problem. FIGS. 3A-B illustrate the correspondence problem in 2D, 3D, respectively. The true marker positions (black dots) are the vertices of a triangle. The tracking pulse-sequence acquires a series of peaks corresponding to the locations of the markers along each projected axis. In general, for N markers and M dimensions, there are a total of N×M peaks. However, while there are only N true marker positions, back-projection of the peaks yields $N^M$ possible marker positions (crosses). The correspondence problem seeks to determine the true marker positions from the possible marker positions, given the locations of the peaks. Without incorporating any prior knowledge, there is no unique solution to this problem.

FIG. 3A shows that three markers (black dots) in 2D (N=3, M=2) yield six peaks (three on each axis). Back-projection onto 2D yields nine possible marker locations (crosses). FIG. 3B shows that three markers in 3D (N=3, M=3) yield nine peaks. Back-projection onto 3D yields 27 possible marker locations.

In this work, we solved the correspondence problem by incorporating three wireless markers into a glasses frame at predefined locations (FIG. 3C, top). Given the known geometrical arrangement of the markers, we can visualize the solution to the correspondence problem (FIG. 3C, bottom). Applying the tracking pulse-sequence to the glasses produces three peaks along each of the physical x, y, and z gradient axes. Each marker is assigned a number (1, 2, 3). In the x-projection, the peaks are numbered (x1, x2, x3) in order of their appearance along the positive x-axis (right-to-left). We then see that peaks x1, x2, x3, will always correspond to the x-coordinates of markers 3, 2, 1, respectively, as long as the markers' locations relative to one another remains constant. The glasses are designed to maximize the separation of the markers along each axis. This guarantees that when the markers are projected onto any axis, their locations relative to one another will remain constant (i.e., their peaks will not overlap or change their locations relative to one another), even under the maximum head rotations)(15-20° possible inside the head coil. Note that translations do not pose a problem, since they do not change the relative marker locations. The result is a simple one-to-one mapping solution to the correspondence problem. Peak searches in all three 1D projections, together with the peak-to-marker assignments in FIG. 3C, thus yield each marker's 3D coordinates.

As shown in FIG. 3C (top), the correspondence problem can be solved by integrating three markers (1, 2, 3) into the glasses at predefined noncollinear locations to form a known geometrical arrangement. FIG. 3C (bottom) shows 3×1D projections of the three markers onto the physical x, y, and z gradient axes. Wireless markers are assigned numbers (1, 2, 3). Peaks are assigned numbers (x1, x2, x3, y1, y2, y3, z1, z2, z3) in order of appearance along each of the positive gradient axes (arrow denotes positive direction). Peaks in each 1D projection are sufficiently separated from neighboring peaks such that they will not overlap under reasonable amounts of head motion. By maintaining a constant relative placement of each marker along each axis, the correspondence problem is then solved by a simple peak-to-marker mapping (dotted lines). For the "resting" glasses orientation shown (5° forward tilt), the distances separating each peak are (peak 3-2, peak 2-1): x-projection=66, 82 mm; y-projection=87, 65 mm; z-projection=21, 44 mm.

B4) Experiment I: Wireless Marker Tracking

A single wired marker was manufactured as a reference to evaluate wireless marker tracking. The wired marker included a solenoid inductor and spherical sample, similar to the wireless marker, but with the following differences: (i) a second capacitor was used to tune and match (50Ω) the resonant circuit; (ii) a PIN diode actively detuned the resonant circuit during RF transmit; (iii) the wired marker was attached via coaxial cable to a custom interface box (Clinical MR Solutions, WI) which then connected to the scanner front-end. The wired tracking signal $S_9$, generated by the same tracking pulse-sequence in FIG. 2A, was received via cable connection between the wired marker and its own designated receiver channel 9.

The wired marker will simultaneously generate both a wired ($S_9$) and wireless ($S_{1-8}$) tracking signal. For a single wired marker, $S_9$ will contain three peaks (one for each orthogonal projection), whose locations are used to calculate a traditional wired position $r^{wired} = [x\ y\ z]^{wired}$. Simultaneously, the wired marker will inductively couple with the head coil to generate $S_{1-8}$. $S_{1-8}$ will also contain three peaks, which provide a wirelessly measured position $r^{wireless} = [x\ y\ z]^{wireless}$. The difference between position measurements based on both wired and wireless tracking signals, $\Delta\varepsilon = r^{wired} - r^{wireless}$, can therefore be compared at the same physical wired-marker location. This allows us to use the well established wired tracking standard to validate our wireless tracking approach.

For head motion, position tracking was only evaluated within the eight-channel head coil. A single wired marker was attached to the tip of a 1 m ruler, and manually moved in a raster-like trajectory throughout the head-coil cavity while maintaining a close proximity to the coil's inner wall. The raster trajectory covered the likely marker locations if attached to the head. The tracking pulse-sequence was continuously executed during the raster trajectory to obtain position measurements (N=256) throughout the entire head-coil volume. For each position, $r^{wired}$ and $r^{wireless}$ were calculated, and the difference $\Delta\varepsilon$ was compared. The raster trajectory was repeated for two orthogonal marker orientations to evaluate any orientation dependence on position tracking and signal coupling. A spherical gel phantom was placed inside the head coil to simulate background signal from an imaged object.

B5) Experiment II: Wireless Marker RF Safety

A key motivation to move from wired to wireless markers is improved RF safety by eliminating the need for electrically conducting cables. However, while wired markers are actively detuned during RF transmit via a DC bias signal directly from the scanner, this is not possible for wireless markers. Instead, crossed diodes (e.g., 108a and 108b on FIG. 1) were used to passively detune the wireless markers. This limits the current flow, thereby maintaining $B_1$ homogeneity and eliminating RF safety concerns. To validate this approach, we performed $B_1$ mapping using a spiral Bloch-Siegert $B_1$ mapping sequence on a spherical gel phantom, and in vivo. For the phantom experiment, two wireless markers were directly attached to both sides of the phantom at symmetric locations. The crossed diode was removed from one of the wireless markers to verify its effectiveness. After general patient safety was assured in phantom experiments, $B_1$ mapping was performed in vivo. For in vivo experiments, the subject wore the glasses containing three wireless markers. For safety reasons in vivo, all three wireless markers used crossed diodes.

Direct temperature measurements were also made to rule out significant RF heating in the wireless-marker components. Two wireless markers were tested, with and without crossed diodes. A high RF duty-cycle FSE pulse-sequence was used to image the wireless markers attached to the spherical gel phantom, while temperature was recorded using a Luxtron fiber optic temperature monitor (LumaSense Technologies, CA). Fiber optic probes were directly attached to the inductor and capacitor on each wireless marker.

B6) Experiment III: Motion Range

The separation of marker peaks is important for solving the correspondence problem, as overlapping peaks would lead to incorrect position and/or orientation information and failed prospective correction. To validate the setup, three subjects were instructed to perform the maximum head rotations possible about each of the three axes. The eight-channel head coil was used together with foam padding. After each rotation, the subject was instructed to remain still while a standard 3D-FGRE localizer was performed [field-of-view (FOV)=260 mm$^2$, N=256×128, echo time (TE)/pulse repetition time (TR)=1.8 ms/5.6 ms, slices/thickness=three slices in each of three orthogonal planes/5 mm]. Image registration was used to determine the motion that occurred between each localizer.

These motion ranges were then compared to the maximum theoretical rotations possible with the polycarbonate glasses. Theoretical values were calculated as the maximum rotation about each axis before peak overlap. This was done using basic trigonometry, given the known distances in the x, y, and z directions between each marker (as described above in connection with FIG. 3C). For example, an x-axis rotation of only +15° (head looking up) will cause a peak overlap due to the relatively small marker separation in the z-projection.

B7) Experiment IV: Prospective Motion Correction

Prospective motion correction using the glasses was implemented in a 2D-SE scan (FOV=260 mm$^2$, N=240$^2$, TE/TR=90 ms/1500 ms, slices/thickness/gap=8/5 mm/5 mm). The tracking pulse-sequence (FIG. 2A, rejection threshold=1 mm/1°) was inserted between every imaging phase-encode, and wireless marker positions were measured using $S_{1-8}$ and the peak-to-marker assignments in FIG. 3C. The six degrees-of-freedom transform was calculated that realigns the current marker positions to the original (reference) positions at the beginning of the scan. This transform was then applied to update the image-volume orientation and position before the next imaging phase-encode was acquired.

Two cases were tested on a grid phantom: (i) resting; (ii) performing a deliberate, abrupt in-plane rotation $R_x \sim 10°$ of the phantom in the middle of the scan.

Two cases were tested on a single subject: (i) resting; (ii) performing a series of six deliberate, abrupt head rotations at 45 s intervals throughout the scan: $+R_x$, $-R_x$, $+R_y$, $-R_y$, $+R_z$, $-R_z$.

For each case, two scans were acquired—with correction ON and OFF. For scans with correction OFF, all tracking and six degrees-of-freedom calculations were logged—but not applied to update the image-volume—to verify reproducibility of phantom or subject motion.

C) Results

C1) Experiment I: Wireless Marker Tracking

The raster trajectory was well reproduced for both orientations, and covered the range of reasonable marker locations and orientations during brain MRI. Marker positions measured using the wireless vs. wired tracking signals were virtually identical, despite the lower wireless tracking SNR (signal to noise ratio). Histograms of the difference $\Delta\epsilon$, plotted separately for each x, y, z component in both orientations, all closely follow Gaussian distributions with $\sigma$<0.01 mm, which is comparable to the precision of the tracking technique determined in previous studies.

C2) Experiment II: Wireless Marker RF Safety $B_1$ maps of the phantom and in vivo showed that $B_1$ homogeneity was unaffected near the markers with crossed diodes, indicating that the markers with crossed diodes do not cause any significant flip angle perturbations or artifacts. In contrast, $B_1$ maps of the phantom showed significant $B_1$ distortions near the marker without crossed diodes.

Figure 4:
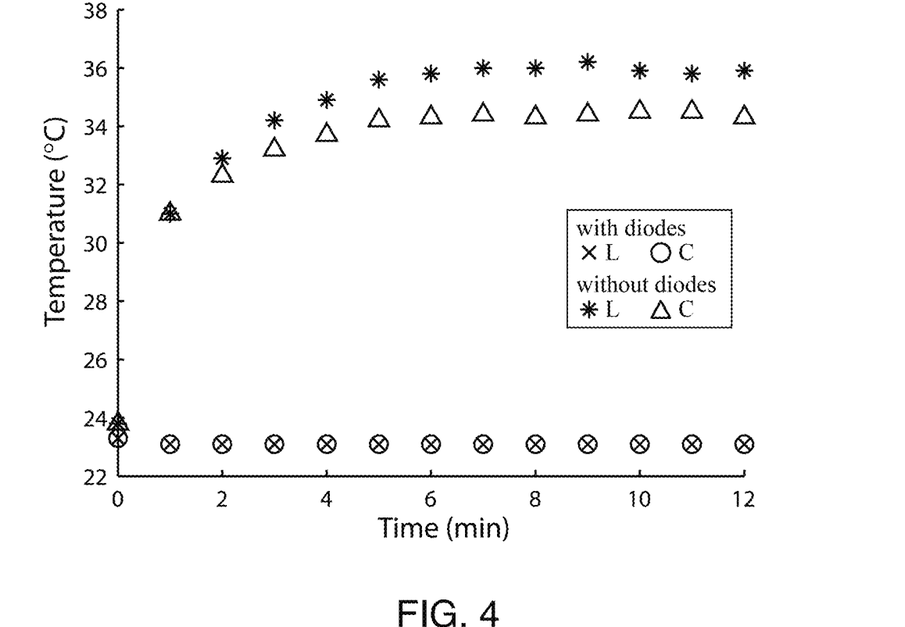
FIG. 4 shows measured temperature in markers with and without crossed diodes over the course of an MRI scan.

FIG. 4 shows temperature measurements on two different wireless markers, with (crosses and circles) and without (* and triangles) crossed diodes, over a 12 min FSE scan. Temperature probes were directly attached to the solenoid inductor 104 and capacitor 106 of each marker. Temperature probes (FIG. 4) placed on the marker with crossed diodes showed no temperature increase (<0.1° C.) over a 12 min FSE scan, indicating that crossed diodes were effective in limiting current flow and preventing device heating. Meanwhile, the marker without crossed diodes experienced temperature increases of 10-12° C.

C3) Experiment III: Motion Range

Maximum achievable rotations were greatest about the z axis (head shaking) with one subject achieving rotations of ±14.9°. Rotations about x (nodding) reached ±11.1°, while rotations about y (head tilt) were only ±6.0°, as this motion was physically uncomfortable to perform. These maximum achievable rotations are within the theoretical tracking range of the glasses, and can therefore be corrected using this setup.

C4) Experiment IV: Prospective Motion Correction

Figure 5:
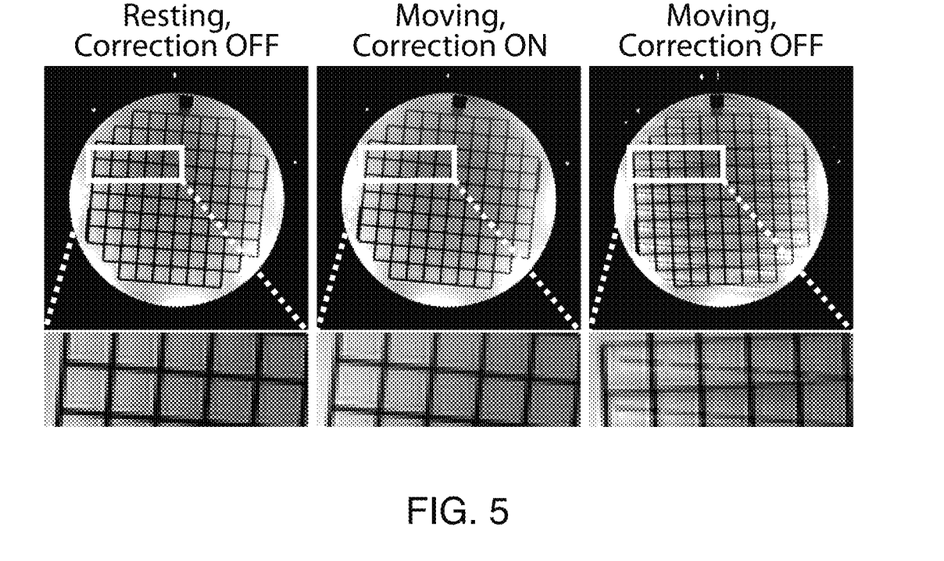
FIG. 5 shows motion correction results for a grid phantom.

FIG. 5 shows phantom images for the resting, motion-corrected, and motion-corrupted cases (left, center and right, respectively). Without correction, images are significantly corrupted by motion artifacts (right) such as blurring and ghosting. Prospective correction (center) results in virtually perfect correction relative to the resting images (left), with fine edges and details such as grid lines being well preserved.

Figure 6A:
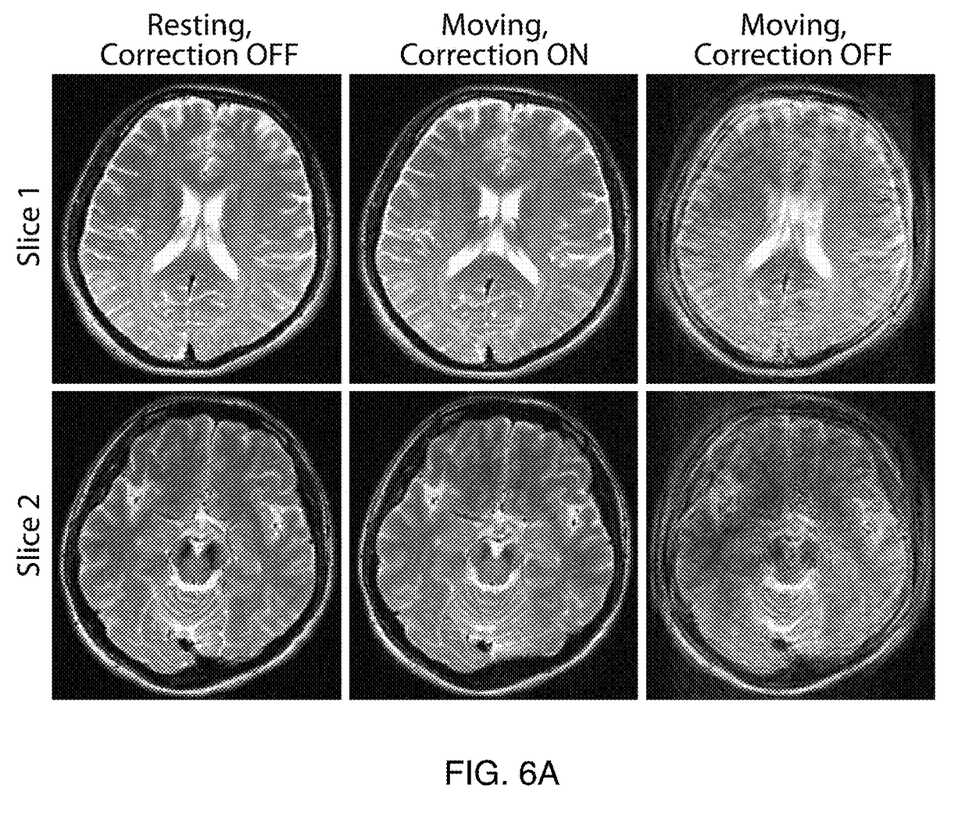
FIGS. 6A-B show motion correction results for brain images.

FIG. 6A shows brain images at two different slices (row 1, 2) acquired without (column 1) and with (column 2, column 3) deliberate motion. An enlarged view (FIG. 6B) of the fine structural details in slice 1 is also shown. The motions were comparable between scans with correction ON (column 2) vs. OFF (column 3). The [minimum, maximum] rotations around each axis were calculated from the wireless marker tracking data as: with correction ON: $R_x$=[−3.4°, 5.2°], $R_y$=[−5.7°, 6.3°], $R_z$=[−3.5°, 4.0°]; with correction OFF: $R_x$=[−4.0°, 5.9°], $R_y$=[−7.3°, 6.2°], $R_z$=[−6.3°, 4.2°]. Resting images with correction ON (not shown) are virtually identical to column 1.

Figure 6B:
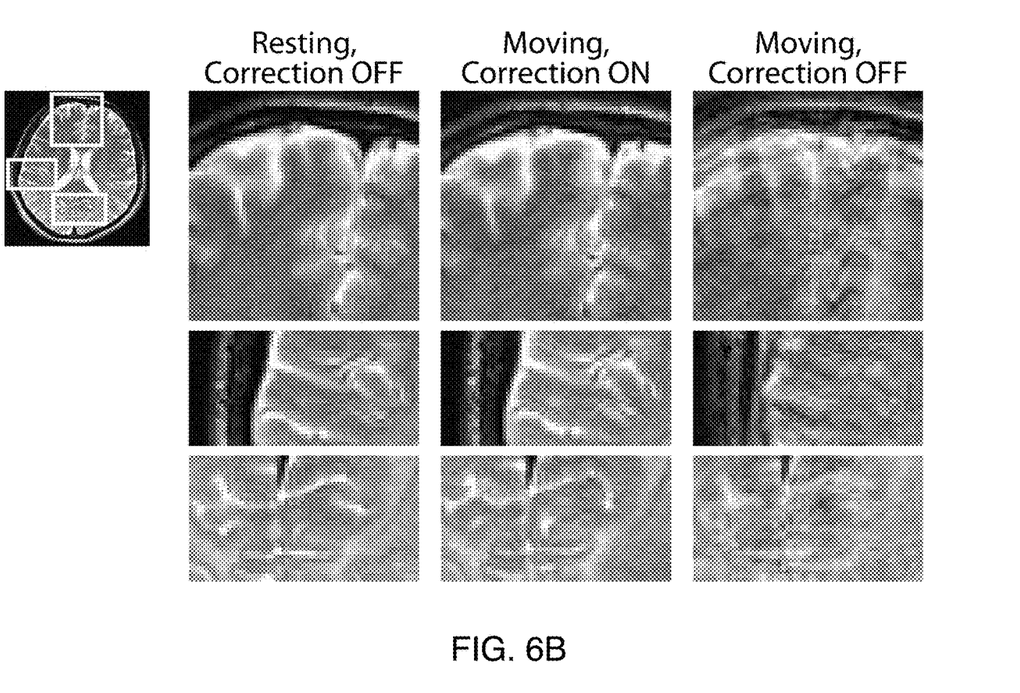

Brain images are shown for the resting, motion-corrected, and motion-corrupted datasets (FIGS. 6A-B). Without correction, images are corrupted by motion artifacts (column 3) such as blurring and ghosting. Prospective correction (column 2) results in virtually perfect correction relative to the resting images (column 1), with fine edges and details of anatomical structures being well preserved (FIG. 6B).

D) Discussion

The familiar and ergonomic glasses design is likely to be well tolerated by patients, and correctly used with minimal instruction. They press on relatively rigid structures, namely the bridge of the nose, and the skull behind the ears, which reduces erroneous marker motion caused by skin movements. They are worn in one unique orientation, and support placement of the markers such that the correspondence problem is easily solved. Previous optical tracking methods have also successfully used glasses as a mount for external markers. Alternative devices are also feasible, such as headbands, headphones, goggles, elastic straps, or rubber swimming caps.

Validation experiments on a grid phantom showed that wired marker tracking within the head coil was accurate to (mm, mean±SD) 0.20±0.14 and 0.24±0.16 along the x and z axes, respectively. Marker positions measured using the wireless vs. wired tracking signal were almost identical, with a difference $\Delta\varepsilon$ comparable to the precision of the tracking technique itself. We therefore expect a similar tracking accuracy for both wireless and wired markers, which is more than sufficient to meet the motion tracking needs for brain MRI. The tracking signal's strength (FIG. 2B) is dependent on the quality of signal coupling between the wireless markers and head coil. Although signal coupling is dependent on the wireless markers' orientation relative to the head-coil elements, $B_0$ and $B_1$, this did not have any practical consequences in our experiments, where the tracking signal was reliable at all times.

RF safety of the wireless markers was verified with $B_1$ maps and by direct temperature measurements. Crossed diodes were effective in limiting current flow in the markers, thereby preventing any local flip angle perturbations, and also preventing device heating. In the event that the crossed diodes failed, they would form a short circuit (RF coil becomes untuned), which is the safe condition. It is unlikely that enough RF current is generated in the small coil to cause this. If an open circuit occurs, most likely from a defective solder joint or mechanical fracture, then a worst-case heating scenario would exist as if no crossed diodes were present. In this case, however, the signal from the marker would be significantly larger than expected if the crossed diodes were intact. This could be detected by the real-time processing algorithm, that expects all marker amplitudes to be very similar and/or below a certain threshold intensity, and faults if one marker abruptly changes. The capsule that encloses each wireless marker is an additional safety measure that prevents skin contact, and also protects the marker from physical impact and detuning.

Prospective motion correction was successfully demonstrated in 2D-SE imaging during bulk head rotations (FIGS. 6A-B). Here, the imaging TE is much greater than the tracking TE and so the Gd-doped spheres were not visible in the images. For sequences where these TEs are comparable (e.g., SPGR, FSE with a short echo spacing), the spheres may appear as bright spots in the images. To reduce the visibility of the spheres in such sequences, a method to better decouple the tracking and imaging signals can be implemented. For example, an ultrashort TE tracking sequence combined with semisolid (i.e., short TO spherical samples could be used. Such a sample would also increase the markers' shelf life. The markers should also be included in the imaging FOV to avoid aliasing. Fortunately, the markers are only millimeters away from the head, so the additional FOV requirements are mostly negligible.

If rotations larger than 15-20° are anticipated, then alternative solutions to the correspondence problem can be considered. The solution described here involves maximizing the separation of the markers in x, y, z, such that their signals will not overlap for the motions in a typical scan (i.e., the order of the marker peaks, which are used to solve the correspondence problem, do not change for the motions in a typical scan). An alternative approach is to perform a brute force search for the marker locations (FIG. 3B, crosses) that best matched the polygon formed by the physical markers (FIG. 3B, black triangle). The matching criteria used in this exemplary implementation was the lengths of the polygon's sides, which is known from the fixed glasses design. However, our initial results suggested that this brute force method lacked the speed, simplicity, and robustness achieved by the final solution described here of relying on a fixed marker signal peak order. Instead of using the sum-of-square signal from the multi-element head coil for wireless marker tracking, another solution may utilize the coil sensitivities from individual elements to differentiate between markers based on their proximity to each element. Also, more than three 1D projections may be used, resulting in additional back projection data so that all markers can be uniquely located (similar to a computed tomography reconstruction)

Other 3D navigator methods [e.g., cloverleaf, PROMO, and EPI] use the head as the reference object for motion tracking, which requires longer measurement and registration times (500 ms) or additional reference scans, and limits their compatibility with many standard imaging sequences. PROPELLER does not correct for the full range of possible head motions. In contrast, in this work the reference object for each wireless marker is a small sphere, which allows full 6-DOF motion tracking using three short 1D projections (15 ms), followed by a computationally simple 3-point 3D-registration algorithm. Because of its small temporal footprint, the tracking pulse-sequence can be flexibly interleaved between single or multiple k-space lines, making it compatible with a wide variety of imaging sequences. Our previous works have interleaved the tracking pulse-sequence into structural and functional imaging sequences, and provide further discussion related to scan-time tradeoffs. Because of the high sensitivity of the wireless markers, flip angles of 1° are sufficient, making the influence on imaging negligible. Unlike optical cam-eras, which also track external markers, wireless markers do not require any cross-calibration since tracking and imaging are performed in the same MR coordinate system. Furthermore, wireless markers are not limited by direct line-of-sight constraints as is needed between a camera and visual marker, allowing them to be effectively used even in the latest closed imaging coil designs. With small modifications, the technique presented here may also be applied to MR-guided interventional devices, or to augment the signal of existing navigator methods, as long as the object to be tracked is near an imaging coil to allow inductive coupling. For example, a single wireless marker may be conveniently placed on the chest to track breathing in body MRI, or on the neck to track/reject swallowing motions in carotid MRI, where placement of traditional pencil-beam navigators is sometimes problematic.

E) Conclusion

Successful prospective correction using wireless-marker tracking is demonstrated that enables high-quality images to be acquired even in the presence of bulk rigid motions. All electrical cables are eliminated by inductively coupling the wireless markers to the head-coil. Wireless markers are a good alternative to wired markers, as they avoid additional RF safety risks from electrically conducting wires, and are not hampered by any mechanical connection to the scanner. This improves ease-of-use for patients and technologists, and minimizes setup times. These practical advantages may lead the way to more widespread adoption of RF coil-based motion tracking in the clinic.

The invention claimed is:

1. A method for tracking the position and orientation of an object in a magnetic resonance (MR) imaging system, the method comprising:
   disposing three or more wireless markers on the object having predetermined and unvarying relative positions, whereby motion of the object causes rigid body motion of a configuration of the three or more wireless markers;
   wherein the wireless markers each include an MR-visible sample coupled to a resonant circuit, and wherein the resonant circuits of the wireless markers are inductively coupled to one or more receive coils of the MR imaging system;
   providing one or more navigator tracking pulses in an MR pulse sequence for motion tracking of the wireless markers on the object;
   receiving marker signals from the wireless markers via the one or more receive coils, wherein the marker signals are responsive to the one or more navigator tracking pulses;
   wherein the marker signals responsive to the one or more navigator tracking pulses include three 1-D projections along three orthogonal directions, wherein the 1-D projections include marker signal peaks from the wireless markers;
   determining a correspondence between the received marker signal peaks and the wireless markers such that the wireless marker responsible for each received marker signal peak in the three 1-D projections is determined, wherein determination of the correspondence relies on knowledge of the predetermined relative positions of the wireless markers, whereby position and orientation information of the object is obtained; and
   providing the position and orientation information of the object as an output or as an input for further processing;
   wherein the wireless markers are separated by distance from each other in each of three orthogonal directions;
   wherein the knowledge of the predetermined relative positions of the wireless markers is used to determine the correspondence from order of the marker signal peaks in the three 1-D projections;
   further comprising performing prospective motion correction of the navigator tracking pulses to keep a relative orientation of coordinates of the navigator tracking pulses and the tracking device within a predetermined range;
   wherein the prospective motion correction of the navigator tracking pulses ensures that orders of the wireless markers in the three 1-D projections do not change, whereby there is no limit to the range of motion that can be tracked.

2. The method of claim 1, wherein the knowledge of the predetermined relative positions of the wireless markers is further used to determine the correspondence by matching possible wireless marker locations according to the three 1-D projections to a constellation of points having the predetermined relative positions of the wireless markers.

3. The method of claim 1, wherein the one or more receive coils are configured as a coil array, and wherein the knowledge of the predetermined relative positions of the wireless markers is further used in combination with a known geometrical layout and sensitivity of the coil array and received strength of the marker signals in the three 1-D projections from individual coil array elements, in order to determine the correspondence.

4. The method of claim 1, wherein the knowledge of the predetermined relative positions of the wireless markers is provided a priori.

5. The method of claim 1, wherein the knowledge of the predetermined relative positions of the wireless markers is provided by a preliminary scan of the wireless markers.

6. The method of claim 1, wherein the navigator tracking pulses comprise gradient echo pulses, spin echo pulses, free induction decay pulses, zero echo time pulses, or pulses having an echo time of 1 ms or less.

7. The method of claim 1, further comprising suppressing the marker signals during parts of the MR pulse sequence that relate to MR imaging.

8. The method of claim 7, wherein the wireless markers each include two diodes connected in parallel with opposite polarities and connected to the resonant circuit such that voltage in the wireless markers is limited.

9. The method of claim 7, wherein the MR-visible samples of the wireless markers have a T2 relaxation time of less than 10 ms.

10. The method of claim 7, wherein the MR-visible samples of the wireless markers have a proton density less than a proton density of tissue being imaged.

11. The method of claim 7, wherein the MR-visible sample has a different resonant frequency than a resonant frequency of tissue being imaged.

12. The method of claim 7, wherein suppressing the marker signals comprises reducing a quality factor of the resonant circuits of the wireless markers during the parts of the MR pulse sequence that relate to MR imaging.

13. The method of claim 1, wherein the object is a subject being imaged.

14. The method of claim 13, wherein the wireless markers are affixed to a tracking device substrate that is selected from the group consisting of: head-mountable devices, headgear, glasses, goggles, headbands, and headphones.

15. The method of claim 13, further comprising using the position and orientation information of the object to perform prospective motion correction for MR imaging.

16. The method of claim 13, further comprising using the position and orientation information of the object to perform retrospective motion correction for MR imaging.

17. The method of claim 1, wherein the object is an interventional device.

18. The method of claim 17, wherein the interventional device is selected from the group consisting of: a needle, a catheter and a surgical instrument.

19. The method of claim 17, further comprising using the position and orientation information of the object to perform MR guided intervention.

* * * * *